(12) United States Patent
Paakinaho et al.

(10) Patent No.: US 11,524,094 B2
(45) Date of Patent: Dec. 13, 2022

(54) POROUS COMPOSITE MATERIAL

(71) Applicant: Biomendex Oy, Tampere (FI)

(72) Inventors: Kaarlo Paakinaho, Pirkkala (FI); Minna Kellomäki, Kangasala (FI)

(73) Assignee: Biomendex Oy, Tampere (FI)

( * ) Notice: Subject to any disclaimer, the term of this patent is extended or adjusted under 35 U.S.C. 154(b) by 557 days.

(21) Appl. No.: 16/334,382

(22) PCT Filed: Sep. 19, 2017

(86) PCT No.: PCT/FI2017/050660
§ 371 (c)(1),
(2) Date: Mar. 19, 2019

(87) PCT Pub. No.: WO2018/050969
PCT Pub. Date: Mar. 22, 2018

(65) Prior Publication Data
US 2021/0228778 A1 Jul. 29, 2021

(30) Foreign Application Priority Data
Sep. 19, 2016 (FI) ..................................... 20165699

(51) Int. Cl.
| | |
|---|---|
| *A61L 27/56* | (2006.01) |
| *A61L 27/36* | (2006.01) |
| *A61L 27/38* | (2006.01) |
| *A61L 27/44* | (2006.01) |
| *A61L 27/46* | (2006.01) |
| *A61L 27/54* | (2006.01) |
| *A61L 27/58* | (2006.01) |

(52) U.S. Cl.
CPC ............. *A61L 27/56* (2013.01); *A61L 27/365* (2013.01); *A61L 27/3616* (2013.01); *A61L 27/3804* (2013.01); *A61L 27/3847* (2013.01); *A61L 27/446* (2013.01); *A61L 27/46* (2013.01); *A61L 27/54* (2013.01); *A61L 27/58* (2013.01); *A61L 2430/02* (2013.01)

(58) Field of Classification Search
None
See application file for complete search history.

(56) References Cited

U.S. PATENT DOCUMENTS

| | | |
|---|---|---|
| 8,119,152 B2 | 2/2012 | Shikinami |
| 2004/0258732 A1 | 12/2004 | Shikinami |

(Continued)

FOREIGN PATENT DOCUMENTS

| | | |
|---|---|---|
| CN | 1646070 A | 7/2005 |
| CN | 1749319 A | 3/2006 |

(Continued)

OTHER PUBLICATIONS

Dean, L. Blood Groups and Red Cell Antigens, Chapter 1: Blood and the cells it contains, National Center for Biotechnology Information, 2005, pp. 1-9. (Year: 2005).*

(Continued)

*Primary Examiner* — Casey S Hagopian
(74) *Attorney, Agent, or Firm* — Laine IP Oy

(57) ABSTRACT

The present invention relates to porous composite materials and objects such as 3D scaffolds, in particular to bioactive and bioresorbable scaffolds that can be transformed at body temperature.

16 Claims, 4 Drawing Sheets

(56) References Cited

U.S. PATENT DOCUMENTS

| | | |
|---|---|---|
| 2005/0251266 A1 | 11/2005 | Maspero et al. |
| 2008/0206297 A1* | 8/2008 | Roeder ............... C08J 9/36 |
| | | 424/422 |
| 2009/0062821 A1* | 3/2009 | Johnson ............. A61L 27/46 |
| | | 606/151 |
| 2013/0218291 A1* | 8/2013 | Giorno ............ A61L 27/3691 |
| | | 623/23.51 |
| 2014/0187726 A1 | 7/2014 | Andjelic et al. |
| 2015/0132354 A1* | 5/2015 | Roeder ............. A61L 27/56 |
| | | 424/423 |
| 2017/0290891 A1* | 10/2017 | Kamakura ......... A61K 9/0014 |

FOREIGN PATENT DOCUMENTS

| | | | |
|---|---|---|---|
| CN | 101648035 A | 2/2010 | |
| CN | 102240415 A | 11/2011 | |
| EP | 1932550 A1 * | 6/2008 | ........... A61L 27/446 |
| JP | 2003159321 A | 6/2003 | |
| JP | 2009136652 A * | 6/2009 | |
| WO | WO2009049650 A2 | 4/2009 | |

OTHER PUBLICATIONS

Vo et al. "The Biomechanics and Optimization of the Needle-syringe System for Injecting Triamcinolone Acetonide into Keloids", Journal of Medical Engineering, 2016, pp. 1-8. (Year: 2016).*

Becker et al: Osteopromotion by a β-Tricalcium Phosphate/Bone Marrow Hybrid Implant for Use in Spine Surgery Spine. vol. 31, Issue 1, Jan. 2006, pp. 11-17.

Shikinami et al: Bioactive and bioresorbable cellular cubic-composite scaffolds for use in bone reconstruction. Journal of the Royal Society, Interface, vol. 3, Aug. 8, 2006, pp. 805-821.

\* cited by examiner

POROUS COMPOSITE MATERIAL

FIELD

The present invention relates to porous composite materials and objects comprising the materials such as 3D scaffolds, in particular to bioactive and bioresorbable scaffolds that can be transformed at body temperature. The present invention concerns also methods for producing the materials and use of the materials in tissue engineering.

BACKGROUND

Bone substitute materials derived from synthetic substances are promising technology challenging the traditional bone grafting in the field of regenerative medicine. An advanced method for bone regeneration is to use tissue engineering methods that combine suitable cells together with bioactive and bioresorbable porous materials, i.e. scaffolds. In order to be used in regenerative surgery, the scaffold has to fulfil several requirements. For example, it should stimulate and support cell proliferation and tissue formation in three dimensional environments.

State of the art implantable porous 3D scaffolds suitable for bone substitute materials comprise either pure ceramic materials or biodegradable and bioabsorbable polymer containing bioactive ceramic particles dispersed therein.

Ideally, scaffolds for tissue regeneration should have the ability to be manipulated intraoperatively in order to adjust to the shape of the defect. Bioceramics are hard but brittle and cannot be easily shaped according the operational need. They also lack packing performance meaning that the optimal packing of particulates cannot be determined during operation. Hard particles do not form an effective interface with the native tissue, because they do not take shape according to the defects shape, i.e. they only form an interface with surrounding tissue from their corners and sharp edges. If porous materials consisting of pure ceramic component are packed roughly, they can break and turn into smaller and denser materials. This can lead to complications during surgical operations and bone healing, because the loose particles cannot be squeezed together such that they would stay on the defect site. In such case the position of the defect can significantly effect on the operation technique, its ease and operation time, because loose and porous particles tend to flow downwards due to gravitation.

EP 1932550A1 discloses a composite porous object which comprises a biodegradable and biosorbable polymer containing bioactive bioceramic particles dispersed therein. Inner parts of the material have large voids having void diameter of 40-600 µm, and small voids having void diameter of 1 µm or smaller.

U.S. Pat. No. 8,119,152 discloses implantable bioactive material comprising organic-inorganic complex porous article in which bioactive bioceramics powder is uniformly dispersed in a biodegradable and biosorbable polymer. The material has continuous pores and the bioceramics powder is partly exposed to the pore inner surface or the pore inner surface and the pore article surface.

US 2013/0218291A1 discloses rigid PLGA/HA hydroxyapatite composite bone grafts and method of making the same. The biomaterial is formed using a gas foaming method. According to a preferred embodiment the composite is produced by combining particles of polymer and bioceramic, in certain ratios and sizes, and loaded into a mold followed by exposure high pressure $CO_2$ and temperature ca 93° C. for 3-4 hours followed by pressure decrease.

Shikinami et al. [J. R. Soc. Interface, 2006, 3, 805-821, doi:10.1098/rsif. 2006.0144] discloses a bioactive and biosorbable cellular cubic containing 70% by weight calcium phosphate in poly-D/L-lactide. According to the authors, the material has similar compressive strength and cellular geometry to cancellous bone. The material was osteoinductive, and it could be modified intraoperatively when heated above the $T_g$ (65° C.) of the polymer.

One disadvantage of the composite 3D scaffolds of the art is that although they can be trimmed by using scissors and scalpels at room temperature, their transformation and insertion into bone defects requires heating the materials above their glass transition temperatures, such as to 70° C. This may cause a heat sock to the site of defect during operation. Furthermore, high implantation temperature makes the material unsuitable for use in methods where the material is to be inserted to the defect together with cells. According to Becker S. et al. (Spine 31, 1 Jan. 2006—Volume 31—Issue 1—pp 11-17 doi: 10.1097/01.brs.0000192762.40274.57) the bone formation is significantly increased when bone forming cells, e.g. from bone marrow aspirate, are impregnated into implantable scaffold. The usability of patient's own cells, harvested during the same surgical operation, accompanied by an osteoconducting or osteopromotive structure material presents a time and cost-effective method for bone surgery.

Accordingly, there is a need for implantable scaffolds that could be transformed at significantly lower temperatures.

SUMMARY

It was observed in the present invention that if certain porous bioactive and bioresorbable scaffold, having overall porosity of 60-80%, includes plurality, typically irregularly shaped, pores having average pore size between 200 and 500 µm, and wherein at least 50% of the pores are connected to each other by channels wider than 5 µm, the scaffold can be modified by immersing into a fluid and/or by warming. Furthermore, the composite material stiffness can be reduced, elastic recovery speed increased, and the bioactive particles exposed from the polymer matrix by dynamically deforming e.g. by compressing the porous composite material of the present invention in a fluid.

In accordance with the invention, there is provided a new method for producing porous composite material, the method comprising providing porous composite material comprising biodegradable and bioabsorbable organic polymer and bioactive particles dispersed therein, wherein overall porosity of the composite material is 60-80%, average pore size is 200-500 µm, content of the bioactive particles in the composite material is 50-80% by weight, and wherein the bioabsorbable organic polymer comprises caprolactone, the bioactive particles are selected from bioceramic particles and bioactive glass particles, and wherein at least 50% of pores of the composite material are connected to each other by channels, wherein width of the channels is at least 5 µm, immersing the porous composite material into a fluid and/or heating at 25-40 C°, squeezing the porous composite material by subjecting to an external force, and releasing the external force.

In accordance with the invention, there is provided also a new method for producing porous composite material, the method comprising for producing composite material, melt mixing biodegradable and bioabsorbable organic polymer and bioactive particles dispersed therein, wherein content of the bioactive particles in the composite material is 50-80% by weight, and wherein the bioabsorbable organic polymer comprises caprolactone, and the bioactive particles are selected from bioceramic particles and bioactive glass particles, forming one or more holes to the composite material optionally filling one or more of the one or more holes with bioactive particles selected from bioceramic particles, bioactive glass particles and mixtures thereof, and for producing porous composite material saturating the composite material with $CO_2$ under conditions wherein $CO_2$ pressure is at least 74 bar and temperature is between 31° C. and melting temperature of crystalline phase of the organic polymer, decreasing the $CO_2$ pressure to 1 bar, and keeping temperature between 31° C. and melting temperature of crystalline phase of the organic polymer.

According to the present invention, the method further comprises immersing the porous composite material into a fluid and/or heating at 25-40 C°, squeezing the porous composite material by subjecting to an external force, and releasing the external force.

In accordance with the invention, there is also provided a porous composite material obtainable by a method according to the present invention.

In accordance with the invention, there is also provided a porous composite object comprising the porous composite material according to the present invention.

In accordance with the invention, there is also provided porous composite material or a porous composite object according to the present invention for use in tissue engineering.

Further aspects of the invention are disclosed in dependent claims.

The verbs "to comprise" and "to include" are used in this document as open limitations that neither exclude nor require the existence of un-recited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

Figure 1:
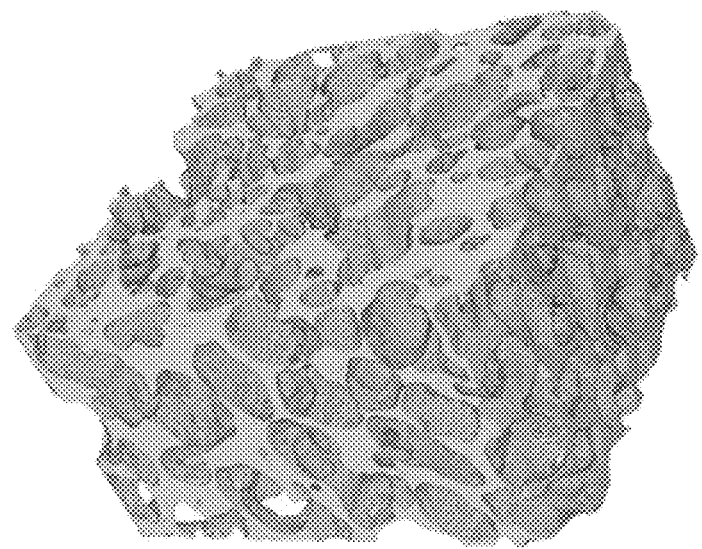
FIG. 1 illustrates a µ-CT photograph of an exemplary porous composite material for use in the present invention.

According to an embodiment the present invention concerns a method for producing porous composite material, the method comprising a) providing porous composite material comprising biodegradable and bioabsorbable organic polymer and bioactive particles dispersed therein, wherein overall porosity of the composite material is 60-80%, average pore size is 200-500 µm, content of the bioactive particles in the composite material is 50-80% by weight, and wherein the bioabsorbable organic polymer comprises caprolactone, the bioactive particles are selected from bioceramic particles and bioactive glass particles, and wherein at least 50% of pores of the composite material are connected to each other by channels, wherein width of the channels is at least 5 µm, (b) immersing the porous composite material into a fluid and/or heating at 25-40 C°, (c) squeezing the porous composite material by subjecting to an external force, and (d) releasing the external force.

At least 50% of the pores of the composite porous material are connected to each other by channels, and that the width of the channels is at least 5 µm, preferably from 50 to 150 µm. This is to ascertain the desired malleability of the object and potential tissue and vascular ingrowth into the object and thus usability in tissue engineering. The porosity can be measured by high resolution micro-computed tomography (µ-CT). In the analysis, the porosity is the total pore volume divided by total volume of the object. The pores can be extracted from the composite phase by thresholding the image stack to form binary image. Open porosity can be defined as all pores that are connected to outside of the object divided by the total volume of the object. The pore network can be assigned so that each pore voxel has a value of the biggest sphere that it belongs to. Porosity is calculated by leaving out pores smaller than the current diameter. The result network is showing pores that are bigger than the current diameter. It means that a particle that has a size of current diameter can access all open porosity pores from outside of the object.

According to one embodiment, the bioceramic particles are granular, and the particles are dispersed homogeneously to the polymer matrix. However, it is also possible that part of the particles is exposed on the pore inner surface and/or the porous object outer surface. This is advantageous for cell attachment and growth.

According to one embodiment the organic polymer comprises, in addition of caprolactone also further components. According to an exemplary embodiment, the biodegradable and bioabsorbable organic polymer comprises caprolactone and one or more of: L-lactic acid, D-lactic acid, D/L lactic acid, glycolic acid, blocks of L-lactic acid and D/L lactic acid, both lactic acid and glycolic acid, both lactic acid and p-dioxanone, both of lactic acid and ethylene glycol.

According to one embodiment the bioceramic particles are selected from a group consisting of unsintered and uncalcinated hydroxyapatite, α-TCP, β-TCP, tetracalcium phosphate, dicalcium phosphate dehydrate, dicalcium phosphate anhydride, and octacalcium phosphate, preferably β-TCP.

The bioactive particles are selected from bioceramic and bioactive glass particles. According to one embodiment, the bioactive particles comprise bioceramic particles. According to another embodiment the bioactive particles comprise bioceramic particles and bioactive glass particles. According to still another embodiment the bioactive particles comprise bioactive glass particles.

The biodegradable and bioabsorbable organic polymers used in the material are preferably those which have ascertained to be safe. The organic polymer comprises caprolactone. Caprolactone monomer is preferable due to its mechanoelastic nature as a component of the polymer chain, as well as its low glass transition temperature. As a structural component in lactide-based polymers, e.g. in poly-lactide-co-ε-caprolactone copolymer comprising 70 molar-% L-lactide and 30 molar-% of ε-caprolactone (70L30CL), the caprolactone parts of the polymer chain generates significantly elastic nature to the material compared to polylactides comprising only L- or D-isomers of lactide.

Exemplary polymers that may be present are polyglycolide (PGA), copolymers of glycolide, polylactides, copolymers of polylactide, unsymmetrically 3,6-substituted poly-1,4-dioxane-2,5 diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohol (PVA), polypeptides, poly-β-malic acid (PMLA), poly-β-alkanoic acids, polyethyleneoxide (PEO) and chitine polymers. Copolymers of glycolide comprise, for example, glycolide/L-lactide copolymers (PGA/PLLA) and glycolide/trimethylene carbonate copolymers (PGA/TMC). Polylactides comprise, for example, poly-L-lactide (PLLA), poly-D-lactide (PDLA) and poly-DL-lactide (PDLLA). Copolymers of polylactide comprise, for example, L-lactide/DL-lactide copolymers, L-lactide/D-lactide copolymers, lactide/tetramethylglycolide copolymers, lactide/trimethylene carbonate copolymers, lactide/δ-valerolactone copolymer, lactide/ε-caprolactone copolymer, polydepsipeptides (glysine-DL-lactide copolymer), polylactide/polyethylene oxide copolymers and polylactide/polyethylene glycol (PEG) copolymers. A particular organic polymer is poly (lactide-co-ε-caprolactone).

Exemplary bioceramic particles comprise unsintered and uncalcinated hydroxyapatite, α-tricalcium phosphate (α-TCP), β-tricalcium phosphate (β-TCP), tetracalcium phosphate, dicalcium phosphate dehydrate, dicalcium phosphate anhydride, octacalcium phosphate or any of bioactive glasses. A particular bioceramic particle is β-TCP. The bioceramic particles and/or the bioactive glass particles are preferably granular, and the granule size is preferably 1-500 μm, more preferably 3-300 μm, most preferably 5-200 μm. The granulation is preferable, since granulate particles have initially sharp edges that release the ions more rapidly than dense smoot surface. Naturally, also other shapes can be used. An exemplary porous composite material comprises β-TCP as the bioceramic material, and polylactide-co-ε-caprolactone as the organic polymer.

According to one embodiment the biomaterial comprises bioactive glass particles. Bioactive glasses are a group of surface reactive glass-ceramic biomaterials and include the original bioactive glass, Bioglass®. Exemplary bioactive glass particles suitable for the present invention are 45S5, 58S, 70S30C, and S53P4.

The composite material used for the present invention is produced preferably my melt mixing. Compared to other methods, e.g. solvent mixing or mixing small particulates, the melt mixing is advantageous, because gravity does generate particle distribution gradient to the composite material. Accordingly, melt mixing of ceramic particles with polymer melt generates an isotropic and homogenous composite base structure, in which the ceramic particles are homogenously distributed throughout the material. This is advantageous also in the foaming phase, because interactions of polymer chains are uniform in the material and disturbance from non-mixed areas which would intervein the pore formation are avoided.

According to an exemplary embodiment the method comprises melt mixing the bioabsorbable polymer and the bioactive material such as bioactive bioceramic particles, for example by extrusion into rod shape, foaming the composite structure into a porous composite structure by supercritical carbon dioxide and cutting the composite foam into desired shaped porous composite object.

According to a particular embodiment, the method of the present invention for producing porous composite material comprises forming, e.g. by drilling one or more holes to the composite object prior to saturating. One or more of the one or more holes may be filled with bioactive particles. Thus, the method enables creating small directed holes in the composite porous object and/or heterogeneous areas into the material with high ceramic surface contact to the aspirated cells or ingrowing tissue.

According to one embodiment the method comprises
  for producing composite material, melt mixing biodegradable and bioabsorbable organic polymer and bioactive particles dispersed therein, wherein content of the bioactive particles in the composite material is 50-80% by weight, and wherein the bioabsorbable organic polymer comprises caprolactone, and the bioactive particles are selected from bioceramic particles and bioactive glass particles,
  optionally forming one or more holes to the composite material
  optionally filling one or more of the one or more holes with bioactive particles selected from bioceramic particles, bioactive glass particles and mixtures thereof, for producing porous composite material,
  saturating the composite material with $CO_2$ under conditions wherein $CO_2$ pressure is at least 74 bar and temperature is between 31° C. and melting temperature of crystalline phase of the organic polymer, and
  decreasing the $CO_2$ pressure to 1 bar, and keeping temperature between 31° C. and melting temperature of crystalline phase of the organic polymer.

The foaming is performed by saturating the non-foamed material with $CO_2$ under conditions wherein $CO_2$ pressure is at least 74 bar and temperature is between 31° C. and melting temperature of crystalline phase of the organic polymer, and decreasing $CO_2$ pressure to 1 bar and keeping temperature between 31° C. and melting temperature of crystalline phase of the organic polymer.

The method of the present invention comprises also the following steps
  immersing the porous composite material into a fluid and/or heating at 25-40 C°,
  squeezing the composite material by subjecting to an external force, and releasing the external force.

Exemplary suitable fluids are alcohol such as ethanol and methanol, water, saline, and body fluid. Preferable body fluids are blood and bone marrow aspirate. According to a particular embodiment the body fluid comprises cells, such as stem cells. An exemplary external force is 0.5-100 N.

According to an exemplary embodiment the method comprises squeezing the material to a nonporous state by using an external force, and then releasing the external force so that the material returns to a porous state and the fluid, in particular body fluid absorbs to pores of the material. An exemplary force is 0.5-100 N.

According to another embodiment the present invention concerns a porous composite material obtainable by the method of the present invention, and an object comprising the material.

According to one embodiment the bioactive particles of the material comprise bioceramic particles. According to a particular embodiment the bioceramic particles are granular, and the particles are dispersed homogeneously to the polymer matrix.

According to another embodiment the bioceramic particles of the material are granular, and part of the particles are exposed on the pore inner surface and/or the porous material outer surface.

According to a particular embodiment the pore inner surfaces are covered by a polymer film, and the polymer film is at least partially broken upon deforming such as squeezing the porous composite material.

FIG. 1 illustrates a μ-CT photograph of an exemplary object made of porous composite material suitable for use in the present invention. The object shown therein was prepared by melt mixing poly-L-lactide-co-ε-caprolactone 70L/30CL (PLCL), and β-tricalcium phosphate (β-TCP) in melt extrusion process with the ratio of 50 weight-% of PLCL co-polymer and 50 weight-% of β-TCP with the granule size 100-300 μm. The composition was extruded into rod shape. The composite rods were cut, placed into rod-shaped molds and foamed with supercritical carbon dioxide ($ScCO_2$). After the composite rods were saturated with $CO_2$ the pressure was decreased to the atmospheric pressure. The processing parameters including time, temperature and pressure were optimized so that the desired pore size, pore connectivity and the channel width was obtained. The parameters affecting the pore generation are time used for $CO_2$ diffusion or saturation into the polymer or composite structure, pressure, depressurization rate and process temperature. The time needed for $ScCO_2$ saturation is between 10 to 120 min, preferably between 40 to 90 min. The pressure needed for generating the pore structure is at least 74 bar, exemplary between 74 bar and 600 bar, preferably between 200 bar and 500 bar and the depressurization rate is in the range from 0.8 bar/min to 10 bar/min, preferably from 1.2 bar/min to 7 bar/min. The temperatures needed for the foaming process are between 31° C. and the melting temperature of the crystalline phase of the polymer. Exemplary temperature for melting the crystalline phase are 130° C. for PLCL 70/30 and 170° C. for P(L/D) LA 96L/4D.

Figure 2:
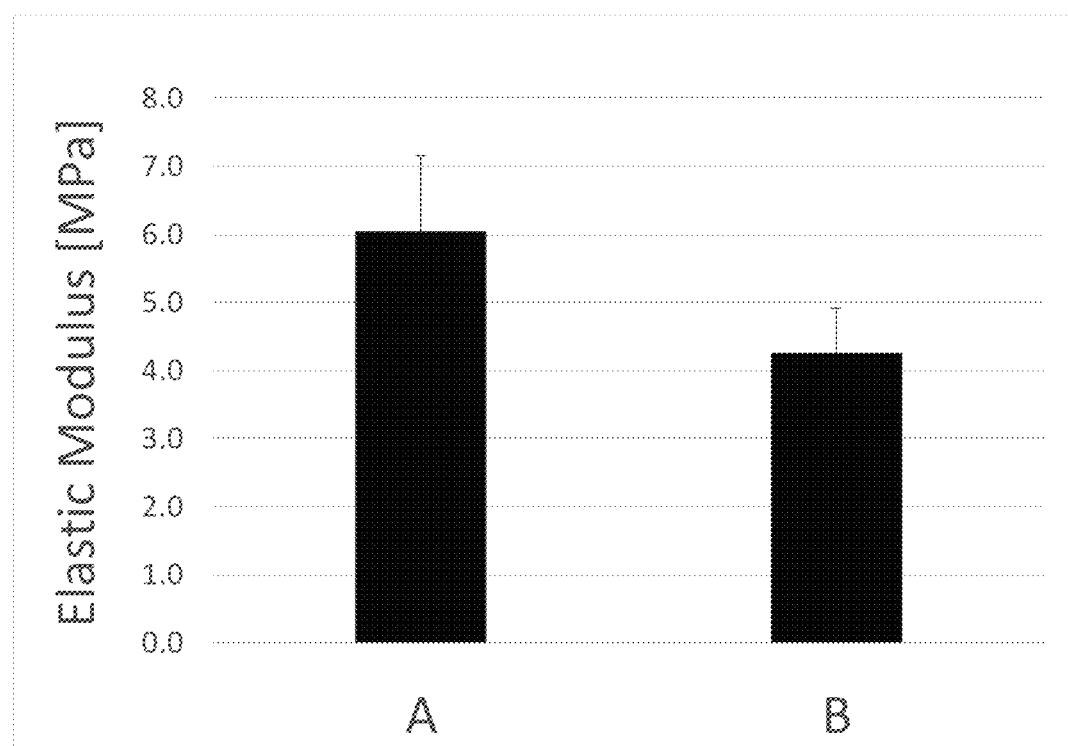
FIG. 2 illustrates the decrease of compression modulus of an exemplary porous composite material when soaked in water (A=dry; B soaked for 48 h at 37° C.)
Figure 3:
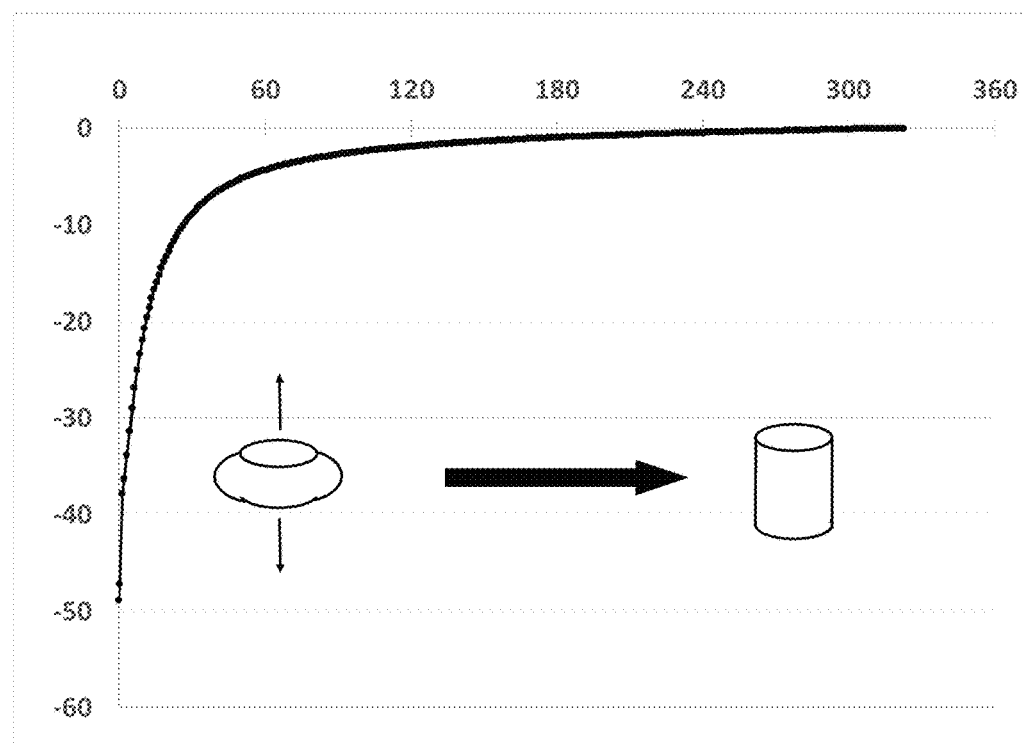
FIG. 3 illustrates the strain/elastic recovery of an exemplary soaked and compressed composite porous material according the present invention.

FIG. 2 illustrates the decrease of elastic modulus when the porous object of FIG. 1 is dynamically compressed after immersing to water, and FIG. 3 illustrates the strain/elastic recovery of soaked and compressed composite porous object. It was surprisingly found that the modulus of the porous composite object of the present invention is lower when exposed to fluid than when dry. Accordingly, the elastic modulus decreased from 6 MPa to 4 MPa, and the material retains its original shape when the compression force is removed. This allows a fluid, in particular body fluid, such as blood and bone marrow aspirate, to be floated in the object. This is advantageous especially during surgical operations when for example bone marrow aspirate or venous blood can be easily soaked to the porous object without additional complex instrumentation.

Figure 4:
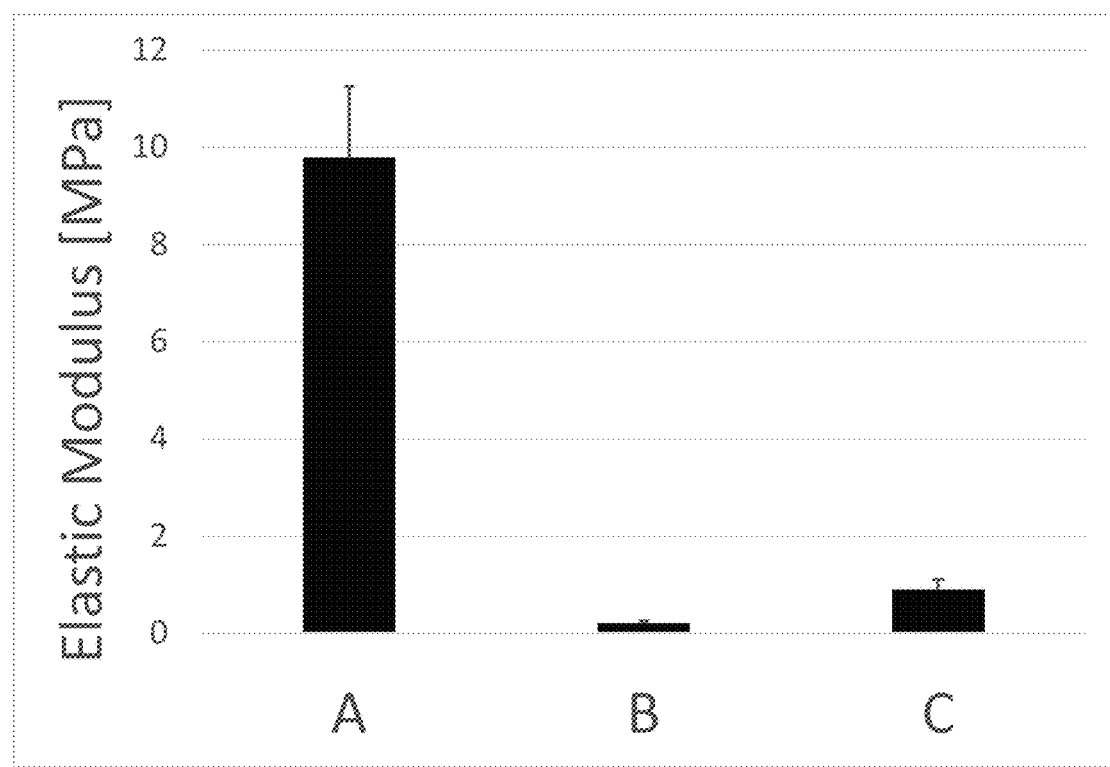
FIG. 4 illustrates the decrease of elastic modulus of an exemplary porous composite material according the present invention (A=dry; B=wet and dynamically compressed for 10 min; C vacuum dried for 3 d after wetting and dynamically compressing)
Figure 5A:
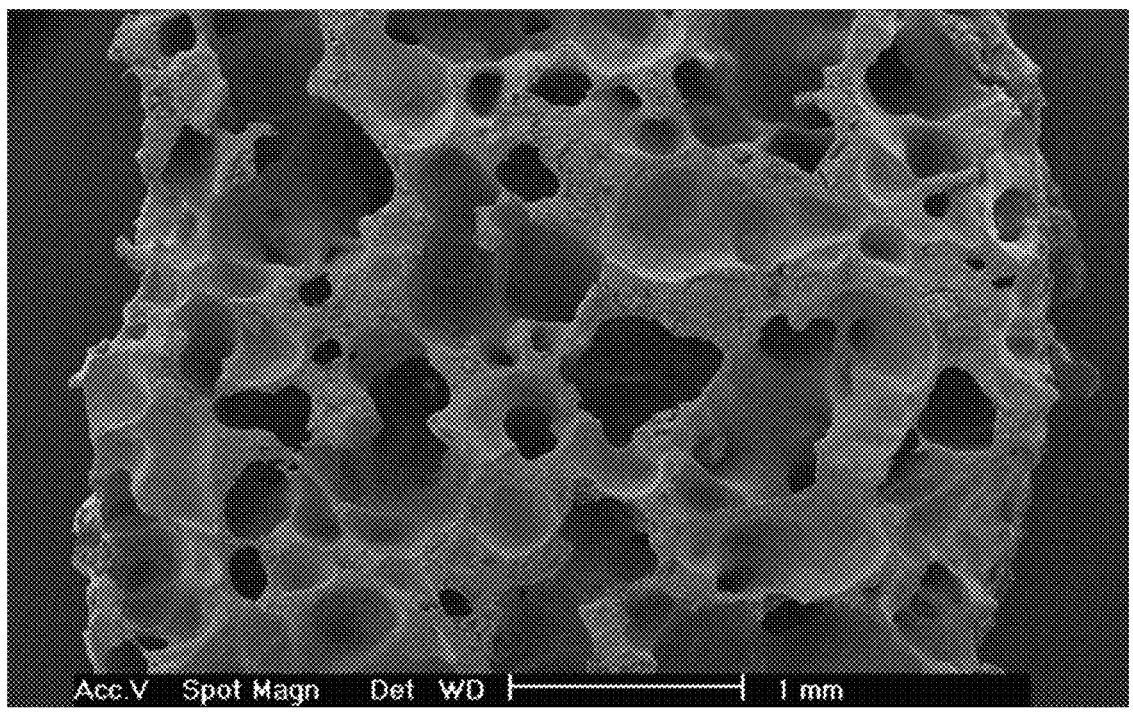
FIG. 5 presents structural changes in an exemplary composite material according to the present invention that occurs during deformation process from structure A (dry) to structure B (after wetting and compressing)
Figure 5B:
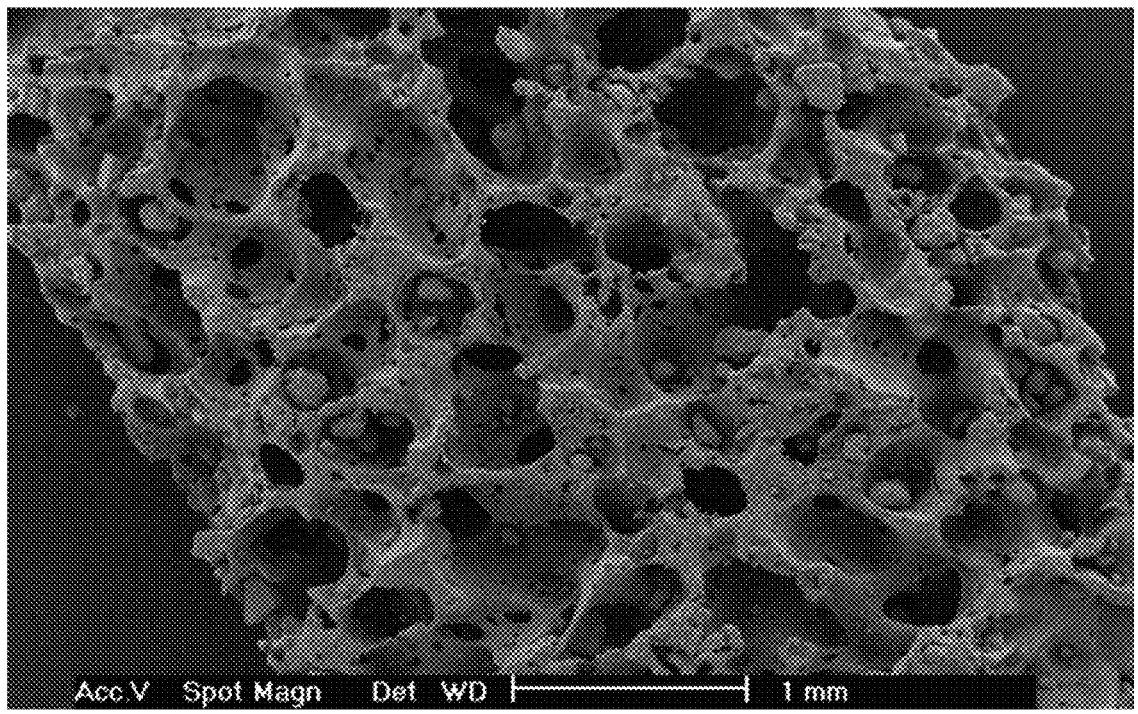

FIG. 4 illustrates the decrease of elastic modulus when the porous composite object is dynamically deformulated by compressing and immersing into water, and FIG. 5 illustrates how the dynamic compression affects the microstructure of the object. In FIG. 4, bar A shows elastic modulus of a dry object. Bar B shows elastic modulus of the object after wetting and dynamically compressing for 10 min. Bar C show the situation when the object is vacuum dried after the wetting and compressing. Accordingly, the modulus is decreased ca. two orders of magnitude. The microstructure clearly changes during dynamic deformation from porous structure with smooth and solid polymer film covering pore surfaces (FIG. 5A) to porous structure with micropores or channels on the pore surfaces and ceramic particles exposed at least partly on the pore surfaces (FIG. 5B). The change in the structure also affects the mechanoelastic properties of the porous composite due to weaker reinforcement of ceramic particles embedded in the polymer phase. The ultimate strength and elastic modulus decreases and the porous composite object significantly softens at temperatures over 25° C. as wet or dry. This enables an effective method to wet the sample by blood or bone marrow aspirate or other body fluid. The at least partly exposed bioactive particles such as bioactive ceramic particles increases biological activity of the porous composite object, because the interaction between the bioactive particles such as bioceramic particles and the cells is more probable.

Figure 6A:
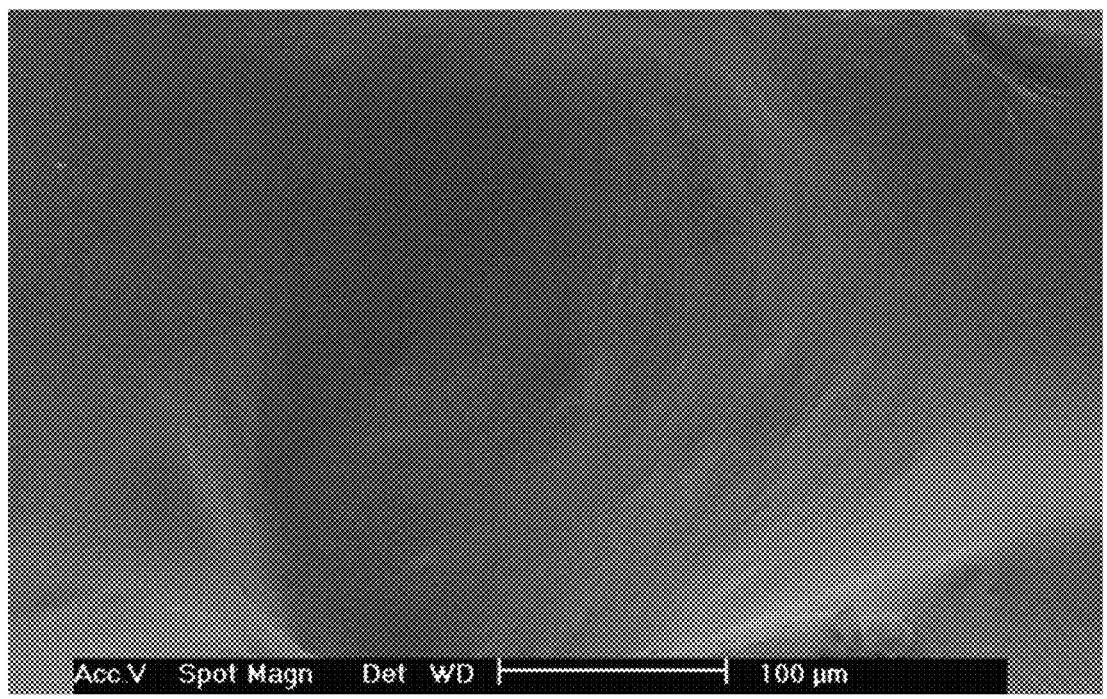
FIG. 6 presents structural change in a pore surface of an exemplary composite material according to the present invention due to the mechanical or dynamical deformation from the non-deformed structure A (pore comprising a polymer film) to structure B (the polymer film broken by external force).
Figure 6B:
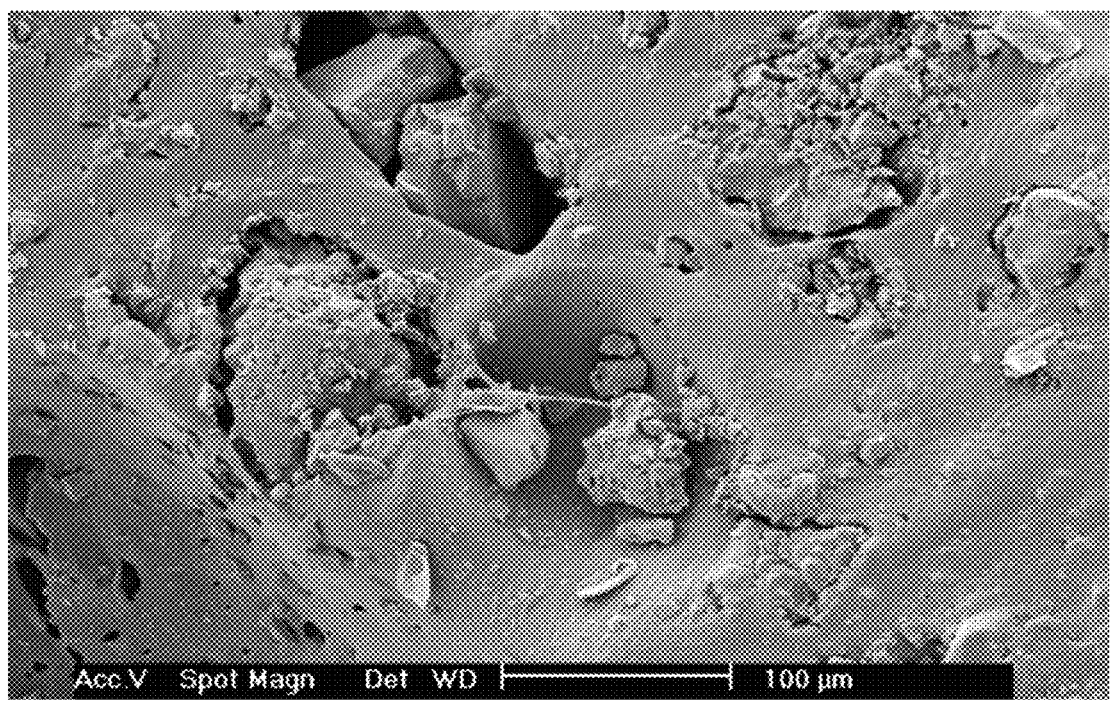

FIG. 6 illustrates a pore of an exemplary composite object, wherein the pore is covered by a PLCL 70L30CL polymer film. FIG. 6A shows a situation wherein the polymer film is intact, and FIG. 6B shows a situation wherein the film has been broken.

Accordingly, the pore inner surfaces of the composite material and object of the present invention may be covered by a polymer film which can be broken by mechanical or dynamic deformation at temperatures ca. 25° C. or higher as dry or wet. Accordingly, as shown in FIG. 6B, at least some of the ceramic particles embedded into the polymer matrix will be exposed or detached from the composite structure or pore surfaces. This transformation of structure upon deformation can be advantageous to the cells proliferation and differentiation and thus tissue regeneration.

The porous composite object of the present invention has preferably a full elastic recovery from 50% compression in about 0.5-60 minutes after compression. This property is advantageous when the object is used e.g. for bone defect correction. Accordingly, the object can be squeezed and inserted into the defect, and while in place, the object is able to fill the defect entirely and form good contact with the surrounding bone tissue. Further advantage is that the structure of the porous composite object of the present invention is that when inserted in the bone defect, protuberances of the object can protrude the surrounding bone pores when the compote material is recovering from compression. When plurality of objects is used for bone defect correction, the protuberances of one object can protrude to the pores of the second object during elastic recovery from compression. This advantageous property enables the formation of continuous porous matrix that is mechanically fused to one porous body.

Example 1

A polymer composite was prepared by melt mixing poly-L-lactide-co-ε-caprolactone (PLCL), with the molar ratio of 70% L-lactide and 30% ε-caprolactone, and β-tricalcium phosphate (β-TCP) in melt extrusion process with the ratio of 50 weight-% of PLCL co-polymer and 50 weight-% of β-TCP with the granule size 100-300 μm. The composition was extruded into rod shape. The mixing ratio was assured by thermogravimetric analysis. The composite rods were cut, placed into rod-shaped molds and closed into a pressure vessel. The vessel was filled with $CO_2$ and the pressure was increased to a range of 74 bar to 600 bar. The composite rods were saturated with $CO_2$ for 30 to 90 minutes after which the pressure was decreased to the atmospheric pressure with the depressurization rate of 1.7 bar/min to 10 bar/min while keeping the temperature between 31° C. and melting temperature of the crystalline phase of the polymer. The porosity and pore size distribution were measured by micro-computed tomography. In the analysis, the porosity is the total pore volume divided by the total volume of the object and the open porosity is defined as all pores connected to outside of the object divided by the total volume of the object. It is typical for the composite to have a distinctive polymer film on the pore surfaces that covers the ceramic particles of composite. The foamed rods were cut to disk shape, packed and gamma-irradiated for sterility. Before implantation the porous composites were submerged to venous blood and dynamically compressed at room temperature. During the wetting and repeatedly compressing or squeezing the porous composite object the modulus decreased and the stiff structure transformed into elastic, fully shape recovering, composite that was to soak the applied blood into it. Simultaneously at least some of the β-TCP particles embedded in the polymer matrix were exposed from the pore surfaces. A μ-CT photograph of an exemplary object prepared according to Example 1 is shown in FIG. 1 and the structural change during the compression is shown in FIG. 5.

Example 2

A polymer composite was prepared by melt mixing poly-L-lactide-co-ε-caprolactone (PLCL), with the molar ratio of 70% L-lactide and 30% ε-caprolactone, and β-tricalcium phosphate (β-TCP) in melt extrusion process with the ratio of 50 weight-% of PLCL co-polymer and 35 weight-% of β-TCP with the granule size 100-300 μm and 15 weight-% of bioactive glass (4555) with the granules size 100-300 μm. The composition was extruded into rod shape. The composite rods were cut, placed into rectangular-shaped molds and foamed with supercritical carbon dioxide. The used foaming process temperatures were between the glass transition temperature and the melting temperature of crystalline phase of the polymer and the pressures were between 500 bar and atmospheric pressure. After the composite rods were saturated with $CO_2$ the pressure was decreased to the atmospheric pressure. The foamed rods were cut into block shape 20 mm×20 mm×6 mm submerged to ethanol for 30 min and then repeatedly compressed with over 50% deformation ratio from different sides in order to expose at least part of the β-TCP and bioactive glass particles from the pore surfaces. The samples were vacuum dried before packing and gamma sterilization. A β-CT photograph of an exemplary object prepared according to Example 2 is shown in FIG. 5B

Example 3

A polymer composite was prepared by melt mixing poly-L-lactide-co-ε-caprolactone (PLCL), with the molar ratio of 70% L-lactide and 30% ε-caprolactone, and β-tricalcium phosphate (β-TCP) in melt extrusion process with the ratio of 40 weight-% of PLCL co-polymer and 60 weight-% of β-TCP with the granule size 100-300 μm. The composition was extruded into rod shape. The mixing ratio was assured by thermogravimetric analysis. The composite rods were cut, placed into rod-shaped molds and foamed with supercritical carbon dioxide. The used foaming process temperatures were between the glass transition temperature and the melting temperature of crystalline phase of the polymer and the pressures were between 500 bar and atmospheric pressure. After the composite rods were saturated with $CO_2$ the pressure was decreased to the atmospheric pressure. The foamed rods were ground into porous granules with the size of 1.4 mm-2.8 mm.

Example 4

A polymer composite was prepared by melt mixing poly-L-lactide-co-ε-caprolactone (PLCL) with the molar ratio of 70% L-lactide and 30% ε-caprolactone, poly-L/DL-lactide with the molar ratio of 70% L-lactide and 30% DL-lactide and bioactive glass in melt extrusion process with the ratio of 40 weight-% of PLCL co-polymer 10 weight-% of poly-L/DL-lactide and 50 weight-% of bioactive glass (45S5) with the granules size 100-300 μm. The composition was extruded into rod shape. The composite rods were cut, placed into rod-shaped molds and foamed with supercritical carbon dioxide. The used foaming process temperatures were between the glass transition temperature and the melting temperature of crystalline phase of the polymer and the pressures were between 500 bar and atmospheric pressure. After the composite rods were saturated with $CO_2$ the pressure was decreased to the atmospheric pressure. The foamed rods were cut into strip shape of 10 mm×20 mm×3 mm. The samples were vacuum dried before packing and gamma sterilization.

According to still another embodiment, the present invention concerns a method for transferring body fluid to the porous composite material of the preset invention, the method comprising
(a) providing the porous material of the present invention,
(b) immersing the porous material to the body fluid obtainable from a subject,
(c) squeezing the material, preferably to a nonporous state by subjecting the material t to an external force, and
(d) releasing the external force so that the body fluid is absorbed to pores of the material.

According to still another embodiment, the present invention concerns a method for transferring body fluid to the porous composite object of the preset invention, the method comprising
(a) providing the porous object of the present invention,
(b) immersing the porous object to the body fluid obtainable from a subject,
(c) squeezing the object, preferably to a nonporous state by subjecting the object to an external force, and
(d) releasing the external force so that the body fluid is absorbed to pores of the object.

Further embodiments are disclosed in the following numbered clauses.

1. A porous composite material obtainable by a method comprising
a) providing composite material comprising bioabsorbable organic polymer comprising caprolactone, and 50-80% by weight bioactive particles selected from bioceramic particles, bioactive glass particles and mixtures thereof, b) saturating the composite material with $CO_2$ under conditions wherein $CO_2$ pressure is at least 74 bar and temperature is between 31° C. and melting temperature of crystalline phase of the organic polymer, c) decreasing the $CO_2$ pressure to 1 bar and keeping temperature between 31° C. and melting temperature of crystalline phase of the organic polymer.

(d) immersing the composite material into a fluid and/or heating at 25-40 C°, (e) squeezing the composite material by subjecting to an external force, and (f) releasing the external force.

2. The porous composite material according to clause 1 wherein the saturating is for 30-90 min.

3. The porous composite material according clause 1or 2, wherein the decreasing $CO_2$ pressure to 1 bar is from 1 bar/min to 10 bar/min.

4. The porous composite material according to any of clauses 1-3, wherein the organic homo- or copolymer comprises caprolactone and one or more of: L-lactic acid, D-lactic acid, D/L lactic acid, glycolic acid, blocks of L-lactic acid and D/L lactic acid, both lactic acid and glycolic acid, both lactic acid and p-dioxanone, both of lactic acid and ethylene glycol.

5. The porous composite material according to any of claims 1-4, wherein the bioceramic particles are selected from a group consisting of unsintered and uncalcinated hydroxyapatite, β-TCB, β-TCP, tetracalcium phosphate, dicalcium phosphate dehydrate, dicalcium phosphate anhydride, and octacalcium phosphate, preferably β-TCP.

6. A porous composite object comprising porous composite material according to any of clauses 1-5.

7. A porous composite object obtainable by a method comprising a) providing a composite object comprising bioabsorbable organic polymer comprising caprolactone, and 50-80% by weight bioactive particles selected from bioceramic particles and bioactive glass particles and mixtures thereof, b) forming, such as by drilling, one or more holes to the object, c) optionally filling one or more of the one or more holes with bioactive particles selected from bioceramic particles bioglass particles, and mixtures thereof, d) saturating the composite object with $CO_2$ under conditions wherein $CO_2$ pressure is at least 74 bar and temperature is between 31° C. and melting temperature of crystalline phase of the organic polymer, e) decreasing the $CO_2$ pressure to 1 bar and keeping temperature between 31° C. and melting temperature of crystalline phase of the organic polymer, (f) immersing the porous composite material into a fluid and/or heating at 25-40 C°, (g) squeezing the porous composite material by subjecting to an external force, and (h) releasing the external force.

8. The porous composite object according to clause 7 wherein the saturating is for 30-90 min.

9. The porous composite object according any of clauses 8, wherein the decreasing $CO_2$ pressure to 1 bar is from 1 bar/min to 10 bar/min.

10. The porous composite object according to any of clauses 7-9, wherein the organic homo- or copolymer comprises caprolactone and one or more of L-lactic acid, D-lactic acid, D/L lactic acid, glycolic acid, blocks of L-lactic acid and D/L lactic acid, both lactic acid and glycolic acid, both lactic acid and p-dioxanone, both of lactic acid and ethylene glycol.

11. The porous composite object according to any of clauses 7-10, wherein the bioceramic particles are selected from a group consisting of unsintered and uncalcinated hydroxyapatite, α-TCP, β-TCP, tetracalcium phosphate, dicalcium phosphate dehydrate, dicalcium phosphate anhydride, and octacalcium phosphate, preferably β-TCP.

The specific examples provided in the description given above should not be construed as limiting the scope and/or the applicability of the appended claims.

The invention claimed is:

1. A method for producing a modified porous composite material, the method comprising:

(a) providing a porous composite material comprising a biodegradable and bioabsorbable organic polymer having bioactive particles dispersed therein, wherein an overall porosity of the composite material is 60-80%, an average pore size is 200-500 µm, and a content of the bioactive particles in the composite material is 50-80% by weight, wherein the biodegradable and bioabsorbable organic polymer is a poly-L-lactide-co-ε-caprolactone copolymer comprising 70 molar-% L-lactide and 30 molar-% caprolactone, wherein the bioactive particles are selected from the group consisting of bioceramic particles, bioactive glass particles, and combinations thereof, wherein at least 50% of pores of the porous composite material are connected to each other by channels, wherein the width of the channels is at least 5 µm:

(b) immersing the porous composite material into a fluid and/or heating at 25-40° C., wherein the fluid is selected from the group consisting of water, saline, and a body fluid, (c) following the immersing and/or heating, squeezing the porous composite material by subjecting the porous composite material to an external force, and (d) releasing the external force.

2. The method according to claim 1, wherein the fluid is a body fluid, and wherein the body fluid is selected from blood and bone marrow aspirate.

3. The method according to claim 1, where the fluid is a body fluid, and wherein the body fluid comprises cells.

4. The method according to claim 1, wherein the bioceramic particles are selected from the group consisting of unsintered and uncalcinated hydroxyapatite, α-tricalcium phosphate (α-TCP), β-tricalcium phosphate (β-TCP), tetracalcium phosphate, dicalcium phosphate dehydrate, dicalcium phosphate anhydride, and octacalcium phosphate.

5. The method according to claim 1, wherein the external force is 0.5-100 N.

6. The method according to claim 1, wherein the bioactive particles comprise β-tricalcium phosphate (β-TCP).

7. The method according to claim 1, wherein the bioactive particles are granular.

8. The method according to claim 1, wherein, in the step (b), the porous composite material is immersed into a fluid.

9. The method according to claim 1, wherein, the step (b), the porous composite material is immersed into a fluid and heated at 25-40° C.

10. A method for producing a modified porous composite material, the method comprising:

(A) melt mixing a biodegradable and bioabsorbable organic polymer and bioactive particles dispersed therein to produce a porous composite material, wherein an overall porosity of the composite material is 60-80%, an average pore size is 200-500 µm wherein a content of the bioactive particles in the composite material is 50-80% by weight, wherein the biodegradable and bioabsorbable organic polymer is a poly-L lactide-co-ε-caprolactone copolymer comprising 70 molar-% L-lactide and 30 molar-% caprolactone, and wherein the bioactive particles are selected from bioceramic particles, bioactive glass particles, and mixtures thereof, and wherein at least 50% of pores of the porous composite material are connected to each other by channels, wherein the width of the channels is at least 5 μm, (B) forming one or more holes to the composite material, (C) optionally filling one or more of the one or more holes with bioactive particles selected from bioceramic particles, bioactive glass particles and mixtures thereof, wherein the method further comprises, for producing the porous composite material, (D) saturating the composite material with $CO_2$ under conditions wherein $CO_2$ pressure is at least 74 bar and temperature is between 31° C. and melting temperature of crystalline phase of the organic polymer, and (E) decreasing the $CO_2$ pressure to 1 bar, and keeping temperature between 31° C. and melting temperature of crystalline phase of the organic polymer, and wherein the method further comprises:

(I) immersing the porous composite material into a fluid and/or heating at 25-40° C., wherein the fluid is selected from the group consisting of water, saline, and a body fluid, (II) following the immersing and/or heating, squeezing the porous composite material by subjecting to an external force, and (III) releasing the external force.

11. The method according to claim 10, wherein the saturating is done for 10 to 120 min.

12. The method according to claim 10, wherein the decreasing the $CO_2$ pressure to 1 bar is done at a rate from 0.8 bar/min to 10 bar/min.

13. The method according to claim 10, wherein the fluid comprises a body fluid, and wherein the body fluid is selected from the group consisting of blood and bone marrow aspirate.

14. The method according to claim 10, wherein the fluid comprises a body fluid, and wherein the body fluid comprises cells.

15. The method according to claim 10, wherein the bioceramic particles are selected from the group consisting of unsintered and uncalcinated hydroxyapatite, α-TCP, β-TCP, tetracalcium phosphate, dicalcium phosphate dehydrate, dicalcium phosphate anhydride, and octacalcium phosphate.

16. A method for producing a modified porous composite material, the method comprising:

(a) providing a porous composite material comprising a biodegradable and bioabsorbable organic polymer having bioactive particles dispersed therein, wherein an overall porosity of the composite material is 60-80%, an average pore size is 200-500 μm, and a content of the bioactive particles in the composite material is 50-80% by weight, wherein the biodegradable and bioabsorbable organic polymer is a poly-L-lactide-co-ε-caprolactone copolymer comprising 70 molar-% L-lactide and 30 molar-% caprolactone, wherein the bioactive particles are selected from the group consisting of bioceramic particles, bioactive glass particles, and combinations thereof, wherein at least 50% of pores of the porous composite material are connected to each other by channels, wherein the width of the channels is at least 5 μm:

(b) immersing the porous composite material into a fluid and heating at 25-40° C., (c) following the immersing and heating, squeezing the porous composite material by subjecting the porous composite material to an external force, and (d) releasing the external force.

* * * * *